United States Patent [19]

Collins et al.

[11] Patent Number: 5,702,896
[45] Date of Patent: Dec. 30, 1997

[54] METHODS FOR IMPROVING THE SENSITIVITY OF HYBRIDIZATION ASSAYS

[75] Inventors: Mark L. Collins, Holden; Cecile Blomquist, Roslindale; Massimo Lombardo, Framingham; John Eldredge, South Dennis, all of Mass.

[73] Assignee: Amoco Corporation, Chicago, Ill.

[21] Appl. No.: 598,142

[22] Filed: Feb. 7, 1996

Related U.S. Application Data

[63] Continuation of Ser. No. 147,906, Nov. 3, 1993, abandoned, which is a continuation of Ser. No. 661,917, Feb. 27, 1991, abandoned.

[51] Int. Cl.$^6$ ................................................ C12Q 1/68
[52] U.S. Cl. ........................... 435/6; 536/254; 935/78
[58] Field of Search .............................. 435/6; 935/77, 935/78; 536/25.4

[56] References Cited

U.S. PATENT DOCUMENTS

| | | | |
|---|---|---|---|
| 4,302,204 | 11/1981 | Wahl et al. | 435/6 |
| 4,751,177 | 6/1988 | Stabinsky et al. | 435/6 |
| 4,767,699 | 8/1988 | Vary et al. | 435/6 |
| 4,818,680 | 4/1989 | Collins et la. | 435/6 |
| 5,118,605 | 6/1992 | Urdea | 435/6 |

FOREIGN PATENT DOCUMENTS

| | | |
|---|---|---|
| 0232967 | 8/1987 | European Pat. Off. . |
| 0265244 | 4/1988 | European Pat. Off. . |
| 0296557 | 12/1988 | European Pat. Off. . |
| 0304184 | 2/1989 | European Pat. Off. . |
| 0305145 | 3/1989 | European Pat. Off. . |
| 0360940 | 4/1990 | European Pat. Off. . |
| 2164403 | 7/1986 | United Kingdom . |
| 2169403 | 7/1986 | United Kingdom . |
| WO 90/10716 | 9/1990 | WIPO . |
| WO 90/12116 | 10/1990 | WIPO . |

OTHER PUBLICATIONS

Morrissey et al Molecular & Cellular Probes (1989) 3: 189–207.
Wood et al Proc Natl Acad Sci. USA (1985) 82: 1585–1588.
Wood et al. P.N.A.S. 82:1585 (1985).
Wood et al P.N.A.S. 82:1585 (1985).
Ausubel et al. in "Current Protocols. in Mol. Biology" John Wiley and sons. N.Y. vol. 1 pp. 6.4.2, Sup 2 (1987).
Morrissey et al. (1989), Nucleic acid hybridization assays employing dA–tailed probes; I. Multiple capture methods, 181 Anal. Biochem. 345–359.
Hunsaker et al. (1989), Nucleic acid hybridization assays employing dA–tailed probes; II. Advanced multiple capture methods, 181 Anal. Biochem 360–370.

*Primary Examiner*—Carla J. Myers
*Attorney, Agent, or Firm*—Norval B. Galloway

[57] ABSTRACT

Methods for improving the sensitivity of hybridization assays which reduce non-specific binding (NSB) and non-specific hybridization (NSH) are disclosed. The methods include a washing method utilizing tetraalkylammonium salts at high temperatures, and release methods in which a probe-target complex is released from a solid support and recaptured. Use of both the washing and release methods results in substantial reduction in NSB and NSH without performing several rounds of release and recapture of the target nucleic acids.

2 Claims, 6 Drawing Sheets

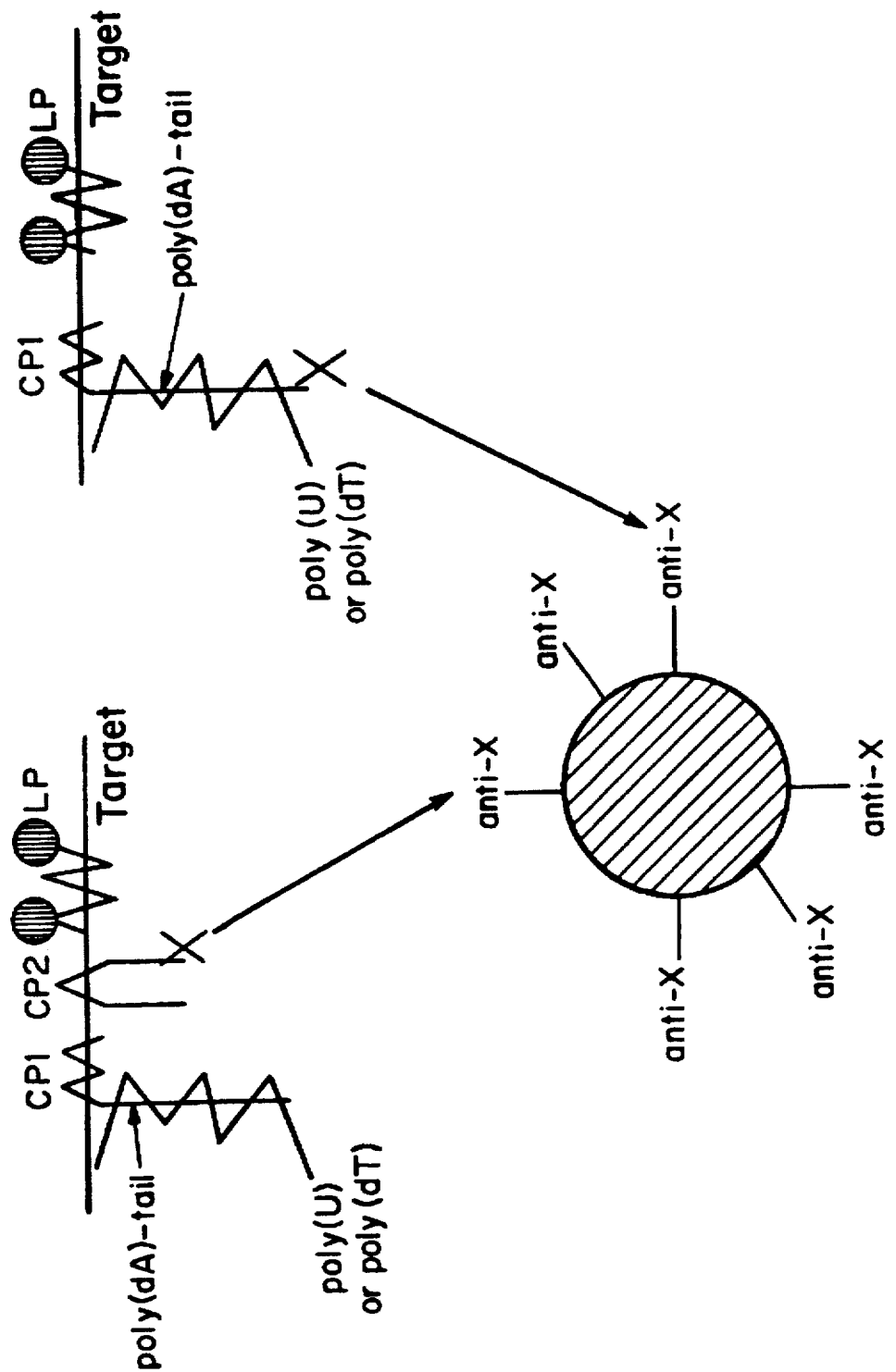

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..35

( x i ) SEQUENCE DESCRIPTION: SEQ ID NO:1:

```
TGT  CCC  CGA  AGG  GAA  AGC  TCT  GTC  TCC  AGA  GTG  GT        35
Cys  Pro  Arg  Arg  Glu  Ser  Ser  Val  Ser  Arg  Val
 1                  5                        10
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Cys  Pro  Arg  Arg  Glu  Ser  Ser  Val  Ser  Arg  Val
 1                  5                        10
```

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..35

( x i ) SEQUENCE DESCRIPTION: SEQ ID NO:3:

```
TCA  ATG  AGC  AAA  GGT  ATT  AAC  TTT  ACT  CCC  TTC  CT        35
Ser  Met  Ser  Lys  Gly  Ile  Asn  Phe  Thr  Pro  Phe
 1                  5                        10
```

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Ser  Met  Ser  Lys  Gly  Ile  Asn  Phe  Thr  Pro  Phe
 1                  5                        10
```

( 2 ) INFORMATION FOR SEQ ID NO:5:

( i ) SEQUENCE CHARACTERISTICS:
        ( A ) LENGTH: 80 base pairs ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..33

( i x ) FEATURE:
        ( A ) NAME/KEY: CDS
        ( B ) LOCATION: 37..54

( i x ) FEATURE:
        ( A ) NAME/KEY: CDS
        ( B ) LOCATION: 58..78

( x i ) SEQUENCE DESCRIPTION: SEQ ID NO:5:

```
TTT  AAT  TCT  TTA  TTC  ATA  GAT  TCT  ACT  ACT  CCT  TGA  CTT  TCT  TCC  CTA      48
Phe  Asn  Ser  Leu  Phe  Ile  Asp  Ser  Thr  Thr  Pro       Leu  Ser  Ser  Leu
 1              5                        10                  1

AAA  AAT  TAG  CCT  GTC  TCT  CAG  TAC  AAT  CTT  TC                                 80
Lys  Asn       Pro  Val  Ser  Gln  Tyr  Asn  Leu
 5              1              5
```

( 2 ) INFORMATION FOR SEQ ID NO:6:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Phe  Asn  Ser  Leu  Phe  Ile  Asp  Ser  Thr  Thr  Pro
 1              5                        10
```

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Leu  Ser  Ser  Leu  Lys  Asn
 1              5
```

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Pro  Val  Ser  Gln  Tyr  Asn  Leu
 1              5
```

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear (ix) FEATURE:
    (A) NAME/KEY: CDS
    (B) LOCATION: 1..24

(xi) SEQUENCE DESCRIPTION: SEQ ID NO:9:

| ATT | CCG | CAC | ATG | TCA | AAA | CCA | GGT | 24 |
| Ile | Pro | His | Met | Ser | Lys | Pro | Gly | |
| 1 | | | | 5 | | | | |

(2) INFORMATION FOR SEQ ID NO:10:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:10:

Ile Pro His Met Ser Lys Pro Gly
1            5

METHODS FOR IMPROVING THE SENSITIVITY OF HYBRIDIZATION ASSAYS

This application is a continuation of application No. 08/147,906, filed Nov. 3, 1993, now abandoned, which is a continuation of U.S. Pat. No. 07/661,917, filed Feb. 27, 1991, now abandoned.

BACKGROUND OF THE INVENTION

Immunoassays have been used for many years in clinical diagnosis, and more recently the utility of hybridization assays in clinical diagnosis is being recognized. In a hybridization assay, specific nucleotide sequences called 'probes' are used to detect the presence in specimens of target nucleic acids such as those of pathogenic viruses or bacteria. These target nucleic acids are generally present at very low levels, thus requiring a very sensitive assay to detect them. Sensitivity, in turn, is a function of the signal-to-noise ratio of the assay. The signal is generally increased by amplification methods, such as those disclosed in Mullis, U.S. Pat. No. 4,683,202. A large variety of methods have been used to reduce assay noise because the sources and types of noise are many, and vary from specimen to specimen.

Hybridization assays take many forms. In traditional filter hybridization methods the target is immobilized on a filter and then probed with a specific labeled probe. Gillespie and Spiegelman, *Journal of Molecular Biology*, 12:829–842 (1965). This method works best with phenol extracted, highly purified nucleic acids. In clinical diagnosis it has the following disadvantages: it traps specimen impurities on the filter; it is limited in specificity (since only one probe must hybridize to generate signal); it is also too slow.

One form of hybridization assay that at least partially overcomes these limitations is called the 'sandwich assay', in which the target is sandwiched between a 'capture' probe and a 'detector' or 'labeled' probe. Ranki et al., U.S. Pat. No. 4,486,539). The sandwich hybrid formed is generally referred to as a 'probe-target complex', consisting minimally of one capture probe, one labeled or detector probe and the target. However, the term 'probe-target complex' can refer to any number of capture probes and any number of labeled or detector probes hybridized to target. The absolute minimum probe-target complex is a binary target-detector probe complex, which is not a sandwich hybrid because it contains no capture probe. The terms 'labeled' and 'detector' probe are used interchangeably to refer to the detectable probe, which is detectable by virtue of possession of a label such as an isotope, biotin, an enzyme, au antiSen, etc.. In another method, the probe contains no detectable label, but is detectable because the detector probe can serve as a target for PCR amplification or as a substrate of an amplification or enzyme reaction, such as Q beta replicase reactions.

In the sandwich assay, the capture probe allows the target to bind to a solid phase. The capture process in turn allows most of the unhybridized probes and the cellular debris and sample impurities to be washed away rather than be trapped within the solid support, as in traditional filter hybridization assays. The labeled or detector probe provides the means of detection.

Excess, unhybridized labeled probe that binds to the solid support is a principal source of the background noise, called nonspecifically bound (NSB) labeled probe. The level of nonspecific binding of probe is often substantially increased by the presence of molecules in the specimen that bind nucleic acids, forming a complex which is tightly bound to the solid support. The other principal source of assay background is termed nonspecific hybridization (NSH). This involves hybridization of one or both of the probes to a molecule termed a "pseudotarget" or "target analogue" that closely resembles a target in sequence. Sandwich assays tend to reduce NSH, as compared to traditional assays, since hybridization of at least two probes to the same molecule is required in order to generate signals. In addition, so called "stringency washes" have been used in the prior art to reduce NSH, in which the solid support is washed at a temperature generally 1–5 degrees (Celsius) below the dissociation temperature of the pseudotarget-oligonucleotide probe complex because the presence of one or more mismatched bases in a oligonucleotide probe-target hybrid substantially reduces the stability of the hybrid. See, e.g., Conner et al., *PNAS*, 80:278–282 (1983) Thus, the stringency wash ideally reduces the amount of hybridization to the pseudotarget while maintaining maximal hybridization to the target. Because better specificity can be achieved with oligonucleotides than with polynucleotides, oligonucleotides are preferred for use as the capture probe and/or labeled probe in sandwich assays.

For simplicity, sandwich assays are generally single step captures. However, without amplification and with oligonucleotides as capture probes, the sensitivity achieved by such single capture step sandwich assays in extremely heterogenous specimens (such as stool) is rarely better than 0.1 femtomole. See, e.g., Morrissey and Collins, *Molecular and Cellular Probes*, 3:189–207 (1989) These assays are limited in sensitivity by NSB, NSH or both. One strategy that has been devised to overcome the limitation in sensitivity due to NSB is called Reversible Target Capture or "RTC". European Patent Application No. 87309308.2; Collins, *Analytical Biochemistry*, Vol. 181, 345–359 and 360–370 (1989), the teachings of which are hereby incorporated herein by reference. In this method, the following cycle is repeated as often as necessary: capture of the target, washing of the support, release of the target. After 4 cycles of the above procedure, as few as 4,400 target molecules have been detected over background, while only about 108 molecules can be detected after one round of capture.

Hybridization assays are becoming increasingly important for clinical applications. Thus, a practical method for increasing the sensitivity of hybridization assays for clinical use by reducing the background noise and, in particular, by increasing the signal-to-noise ratio, would be valuable.

SUMMARY OF THE INVENTION

The present invention relates to rapid methods for substantially reducing non-specific binding (NSB) and non-specific hybridization (NSH) in hybridization assays. The present methods can be generally characterized as washing procedures and release procedures.

The washing method consists of treating the probe-target complex with a high temperature wash after the hybridization step thereby reducing nonspecifically bound probe and reducing nonspecific hybridization of pseudotarget. The present high temperature washing method simultaneously reduces two types of noise, NSB and NSH. This high temperature wash also simultaneously equalizes double-stranded RNA (dsRNA) and double-stranded (dsDNA) hybrids and hybrids of varying GC content. The method improves the signal/noise of RTC, for example, up to 100 fold by reducing non-specific binding (NSB) and non-specific hybridization (NSH). This method is particularly useful for obtaining more specific hybridization and in standardizing assays using both RNA and DNA targets and probes.

The present release procedures consist generally of eluting the target from the solid support and recapturing the target on a second support. The release procedures are introduced after the high-temperature wash to improve elution of the hybridized target nucleic acids. The release methods employ mild physical and chemical conditions to cause specific elution of the target from the support, and provide an improved chemical or thermal elution. These procedures are particularly useful in assays employing reversible target capture (RTC).

In one embodiment, in an assay based on displacement with poly (dT) or poly (rU), the present release method improved the signal-to-noise ratio of RTC up to 40-fold.

Affinity Background Capture (ABC) is another powerful technique for enhancing the signal-to-noise ratio of hybridization assays, particularly RTC. An ABC method which increases the signal-to-noise ratio of RTC is also the subject of the present invention. This method employs adding an affinity-labeled background capture probe to the system in order to hybridize to excess labeled probe which is not associated with a target sequence. The background probe is then captured on an affinity support and removed from the assay system, thereby reducing the background noise caused by the excess labeled probe. In a one embodiment, the background capture probes are prehybridized to the labeled probe. Target, if present, displaces the background capture probes after hybridizing to the labeled probes. Labeled probes not hybridized to target and displaced background capture probes are then removed by a background capture solid phase.

The methods of the invention enhance the sensitivity of hybridization assays by reducing the background noise. The present methods make these assays more selective in the enhancement of signal/noise ratio.

BRIEF DESCRIPTION OF THE FIGURES

FIG. 6 depicts two schemes for recapture of intact probe-target complexes after release method A.

DETAILED DESCRIPTION OF THE INVENTION

Figure 1:
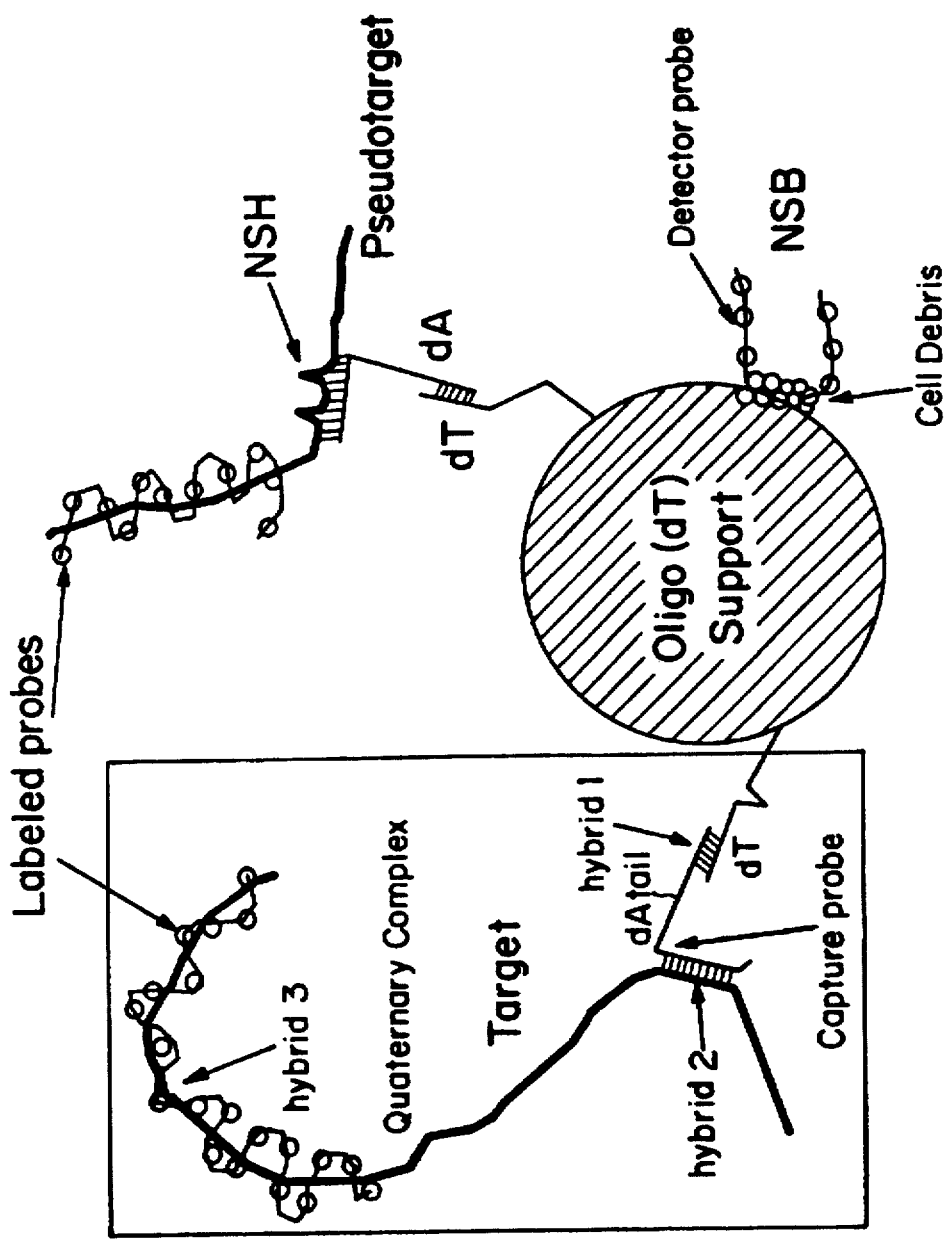
FIG. 1 depicts the quaternary complex, {(labeled probe):(target):(capture probe):(solid phase)}, formed in a RTC procedure along with nonspecifically bound labeled probe (NSB) complexed with cellular debris, and a target analogue (i.e., pseudotarget) that is nonspecifically hybridized (NSH) to the capture probe.

The present invention provides methods for enhancing the effectiveness and specificity of hybridization assays. The present methods can generally be described as high-temperature washing protocols and release protocols, which result in reduced NSH and NSB thereby increasing the sensitivity of the assay. The high-temperature washing protocol of the present method simultaneously reduces NSB and NSH with virtually complete retention of nucleic acid targets bound to an oligo(dT) substrate by the interaction with poly(dA)-tailed capture probes or an oligo(dA) substrate and poly(dT) tailed capture probe. The target can be RNA or DNA, and the probes can be RNA or DNA. Ideally, the RNA and DNA probes would be approximately the same length but could have any GG content. The present washing method involves the use of washes with tetraalkylammonium (TAA) salts or closely related compounds to remove or elute NSB and NSH at an elevated temperature. It has been discovered that the combination of heat-plus-TAA salts preferentially disrupts many of the bonds holding NSB molecules to the support and disrupts the NSH interactions between pseudotarget and the probe while maintaining the hybrid formed between the poly(dA) tail of the capture probe and the oligo (dT) substrate of the solid support.

The term "oligo" is used herein as a prefix to describe nucleic acids which are from about 10 to about 50 nucleotides in length. The term "poly" is used as a prefix for nucleic acids which are greater than 50 nucleotides in length. The present high temperature wash method generally involves the following steps. A hybridization assay is carried out according to the usual procedure for these types of assays, that is, an oligonucleotide capture probe having a nucleotide sequence specific for target DNA or RNA (the capture probe) is added to a sample thought to contain the target sequence (e.g., bacterial DNA for detecting an infection). The capture probe is generally about 15 to 50 nucleotides in length. Hybridization between the target nucleic acid and the probe is allowed to occur. The capture probe has a homopolynucleotide tail, which allows it to be attached to a substrate coated with the complementary homooligonucleotide. In a preferred embodiment of the method, the capture probe is attached to a solid support through the interaction of the homopolynucleotide attached to the probe and the homooligonucleotide substrate coating the solid support. The homopolynucleotide tail on the capture probe is generally 100 to 200 nucleotides in length, and comprises poly (dA), poly (dT) or poly (rU) or poly (rA). The solid support is coated with the complementary homooligonucleotide which is generally about 10 to 20 nucleotides in length. In this method, after the probe-target complex is formed, it is removed from sample impurities by one or more captures on clean solid support. According to the present invention, the complex is then washed with a wash solution which is selected to reduce NSB and/or NSH at an elevated temperature, i.e., above 50° C., which is the reference temperature. The wash is preferably carried out at a temperature of from about 60° to 70° C. A solution containing a tetraalkylammonium salt is used for the wash. Tetraalkylammonium salts which are useful include those having chloride, bromide, phosphate, sulfate, nitrate, trifluoroacetate, thiocyanate, trichloroacetate or acetate counterions. Tetramethylammonium salts are preferred, however trimethyl, triethyl, dimethyl and diethyl ammonium salts can also be used. A concentration of approximately 3.0M is preferred. The washing is generally complete in five minutes or less. In a preferred embodiment of the present washing method, the protocols described herein are followed.

The high temperature wash method is particularly useful with RTC assay systems. RTC is described in detail by Collins in European Patent Application No. 87309308.2 and in *Analytical Biochemistry*, 181:345–370 (1989), the teachings of both of which are hereby incorporated herein by reference.

A hybridization complex formed during a RTC sandwich assay used in the present invention is schematically illustrated in FIG. 1. In the box on the left is the captured probe-target complex referred to as the "quaternary complex". This is a complex between the labeled or detector probe, the target (heavy curved line), the capture probe and the solid support (pictured as a bead). Three hybridizations hold the quaternary complex together: hybrid #1, between the oligo(dT)-solid support and the poly(dA)-tail on the capture probe is ordinarily the weak link in the chain and thus provides for reversibility without disruption of the other hybrids. Thus, reversibility is a rapid and efficient process since there is no need to reform the mixed base sequence hybrids during capture/release cycles. Hybrid #2, which ordinarily supplies the majority of the assay specificity, is that between the unique sequence portion or mixed base sequence of the capture probe and the target and hybrid 3 is that between the labeled (or detector) probe and the target. For convenience, hybridization complexes such as that shown in FIG. 1 are, where necessary, referred to herein according to the following convention: {(detector probe):(target):(capture probe):(solid support)}, where hybridization between individual components of the complex is indicated by colons.

The poly(dA)-tailed capture probe allows the target to bind reversibly to an oligo(dT)-solid phase. As noted above, excess, unhybridized labeled probe that binds to the solid support is a principal source of the background called NSB, or nonspecifically bound labeled probe. It is pictured in FIG. 1 (bottom right) on the surface of the bead as labeled probe complexed with cell debris, but not hybridized to a target or a capture probe. An example of NSH is also depicted in FIG. 1: a pseudotarget (heavy curved line) is pictured as having 2 mismatches (symbolized with a "A") with the (dA)-tailed capture probe, and no mismatches with the detector probe. The methods of present invention provide generic methods for the reduction of both NSH and NSB that are harsh enough to substantially reduce the backgrounds yet fully compatible with the fragile hybrid #1 between poly(dA) and oligo(dT) that reversibly binds the ternary probe-target complex to the solid support.

Two rapid and generic methods for the specific release of support-bound target are disclosed in the above references with the RTC method. Said methods dissociate the poly(dA)-oligo(dT) base pairs (hybrid #1 of FIG. 1) without dissociating the base pairs in the hybrids between the target and the capture probe (#2) and the target and the detector probe (#3). The system was designed this way because disruption of hybrids #2 and #3 would disadvantageously require a relatively slow and inefficient rehybridization during each cycle of the process. The release methods disclosed therein are: (1) chemical release methods such as the use of a buffer containing 2–3M GuSCN at a temperature between 22 and 37 degrees and (2) thermal release methods such as the use of a buffer containing 0.5 m NaCl at a temperature between 55° and 68° C. The methods disclosed therein for the release of target from the support are not completely selective in that a variable fraction (between 20–95%) of the background is also removed with the signal. It is during the recapture that most of the background (between 90 and 99%, depending on the exact conditions of recapture) that eluted with the target (signal) is removed by the RTC procedure.

Previous work with RTC had shown that thermal elution elutes more background, and more signal, than any other form of elution. Heat plus detergent disrupts many of the bonds holding nonspecifically bound molecules to the support and thus solubilizes much of the total assay NSB. It is, however, mot practical to apply a lot of heat (e.g., greater than 50° C.) to the solid support in the ordinary high salt buffers of the prior art because the poly(dA)-oligo(dT) hybrids (shown as hybrid #1 of FIG. 1) will dissociate first, causing an unproductive loss of signal as well as a loss of noise.

Tetraalkylammonium salts are particularly preferred salts for use in the present high temperature washing method because they equalize GC and AT base pairs. Melchior and von Hippel, (1973), Proc. NACl. Acad. Sci. USA, 70:298–302. Thus, with a battery of probes of approximately the same length, a single wash temperature can be used to enforce stringent hybridization on all probes regardless of GC content. Collins and Morrissey, U.S. Ser. No. 07/321,728. This can be very useful in standardizing the washing conditions of a hybridization assay such as RTC.

Another extremely useful and unique property of tetraalkylammonium salts is that they are strong denaturants of double-stranded RNA. Wetmur et al., (1981), Biochemistry, 20:2999–3002. At an appropriate concentration these salts can theoretically be made to be approximately GC/AT and RNA/DNA equivalent. This can be exploited to provide additional specificity with sandwich assays employing DNA-DNA, RNA-DNA hybrids and RNA-RNA hybrids. If the probe lengths are approximately the same, the double-stranded (ds) RNA hybrids will be so strong in most wash buffers that they will likely be stronger than the DNA-RNA hybrids even if the dsRNA hybrid is between the probe and pseudotarget. This means that signal (which is dependent on the DNA-RNA hybrid too) will be lost in the process of washing away the NSH in the dsRNA hybrid to the pseudotarget. This situation is even more acute in RTC because the hybrid between the oligo(dT)-bead and the dA-tailed capture probe (#1) is much weaker than the typical RNA-DNA oligonucleotide hybrid. It would thus appear to be unlikely that wash conditions can be found to make dsRNA hybrids highly specific with RTC.

One way to increase the specificity of dsRNA hybrids in a system that also employs DNA-DNA hybrids and DNA-RNA hybrids is to reduce the length of the RNA probe. However, this would reduce the major advantages of use of RNA probes (over DNA probes) that of speed and efficiency of hybridization and moreover it would necessitate the use of two different RNA probes when both DNA and RNA molecules of the same sequence are targets, as is done in viral assays, with DNA measuring the amount of virus present, and RNA measuring the amount of viral activity. A better solution is to use approximately the same length DNA and RNA probes for the hybridizations and to use tetraalkylammonium salt washes to equalize the strength of the GC and AT base pairs and the dsRNA, dsDNA, and RNA-DNA hybrids of variable GC content simultaneously. Another possible solution is to use modified bases to generate the GC/AT equivalence (as described in Huynh-Dinh and Igolen, U.S. Pat. No. 4,842,996) and to use tetraalkylammonium salts to generate the RNA/DNA equivalence for the purpose of standardizing wash conditions in an automated format, where a multiplicity of washing protocols would be undesirable.

Because of the equalization of the strength of the GC and AT base pairs using tetraalkylammonium salts, oligo(dT)14-poly(dA) is expected to have the stability of a typical 14 mer in these buffers. Wood et al., (1985), Proc. NaCl. Acad. Sci. USA, 82:1585–1588. Surprisingly, however, the strength of the oligo(dT)-poly(dA) hybrid is far greater than expected in TAA salts. Collins and Morrissey, U.S. Ser. No. 07/321,728. In one embodiment using tetraalkylammonium chloride, (TEACl), for example, the dissociation temperature (Td) of the homooligomer is 48° C. (with a 5 minute denaturation time) rather than approximately room temperature, as expected for a 14 mer. This surprising discovery means that TAA salts are candidates for background reducing buffers with RTC because they strengthen the weak link in the quaternary complex that is, the (poly(dA)—oligo(dT) affinity pairs, while allowing pressure to be applied simultaneously to remove NSB and NSH. Tetraethylammonium (TEA) salts are appropriate for washes that reduce NSH, but generally not for NSB, because these washes are performed at a temperature of around 37° C. (for a 33 mer). This is too low to cause a substantial reduction in NSB above and beyond what washes in GuSCN cause at 37° C. Nucleic acids in tetramethylammonium (TMA) salts generally have about a 20°–30° C. higher Td than in TEA salts. Melchior and von Hippel, (1973), Proc. NaCl. Acad. Sci. USA, 70:298–302 and thus are candidates for a combined high temperature NSB-reducing wash and a high temperature NSH-reducing wash. In addition, as indicated above, this wash could be used to equalize both GC/AT base pairs and essentially equalize the strength of both dsRNA and dsDNA. This is extremely advantageous in standardizing washing conditions in automated assays where both RNA and DNA probes and RNA and DNA targets with a wide range of base compositions are used.

In the preferred method of performing RTC, the probe lengths (RNA and DNA) are chosen to be approximately the same. Hybridization would be in a near equivalence buffer such as GT3. Kearney, Collins, Morrissey and Eldredge, (1989), "Hybridization Promotion Reagents", U.S. Ser. No. 333,656,) and universal washing conditions would be used to enforce stringency on all of the hybrids in the system simultaneously. A generic regimen involving both low temperature and high temperature washes would be most advantageous in order to achieve the broadest possible spectrum of NSH reduction and NSB reduction. High temperature, e.g., is best for removing NSB and additionally selects best against the pyrimidine-pyrimidine mismatches (Aboul-ela et al., (1985), Nucleic Acids Res., 13:4811–4824) However, low temperature washes with appropriate salts such as TEA salts are preferred over high temperature TMA salt washes for removing mismatched dsRNA hybrids. Wetmur et al., (1981), Biochemistry, 20:2999–3002.

Alternatively, a single wash employing mixture of tetramethylammonium and tetraethylammonium salts could be used or a wash with a single mixed salt could be used, such as dimethyl diethyl ammonium salts.

Accordingly, many different tetramethylammonium salts (TMA salts) were prepared for evaluation as high temperature wash buffers, including TMA salts containing chloride, acetate, nitrate, thiocyanate, EDTA, sulfate, phosphate, formate, borate, and citrate counterions. All of them were found to significantly improve the signal-to-noise of RTC hybridization assays by reducing both NSB and NSH.

The above-described washing step can be followed by one or more of the release methods described below. The combinations of the wash and release method is particularly effective in improving the singal-to-noise ratio of hybridization assays.

Several release methods for reducing NSB and/or NSH and for reducing the background noise in hybridization assays utilizing displacement hybridization are also the subject of the present invention. For simplicity, the release methods will be referred to as release methods A, B and C.

In release method A, {(detector probe):(target): (capture probe)} ternary complexes are released completely intact from oligo(dT) or oligo(dA) beads using homopolymers such as poly(rU), poly(rA) poly(dA) or poly(dT). The technique is rapid (5 minutes or less), generic (the same displacing molecule will work for all RNA and DNA capture probes, all RNA or DNA targets, and all RNA and DNA labeled probes), and efficient. The intact ternary complex is recapturable for further background reduction on other affinity supports. To provide for recapture after release method A, the initial hybridization can be set up with either two capture probes (particularly when additional specificity is needed), one with a poly(dA) tail and the other with a second affinity ligand (e.g., biotin) or a single specific capture probe can be used that contains two affinity ligands such as poly(dA) and a biotinylated nucleotide.

Release method A generally involves the following steps. RTC is performed according to the usual procedure. The beads are carefully washed in Release A buffer minus the release agent. NSB which is bound to the last solid support is then reduced by displacing the probe-target complex from the solid support. A molar excess of the releasing or displacing probe is used. The solid support can then be removed from the solution, and the free {(capture probe):(target): (detector probe)} ternary complex is measured (see FIG. 5). In one embodiment, the displacing probe can contain an affinity ligard, such as biotin, and the complex formed from the displacing probe and the {(capture probe):(target): (detector probe)} ternary complex can then be recaptured on a solid support bearing the affinity ligand (see FIG. 6). The displacing probe is generally larger than the (dA) or (dT) tail on the capture probe, preferably about 200–400 bp long. All of these release methods result in a significant increase in the signal-to-noise ratio of the RTC process.

Figure 5:
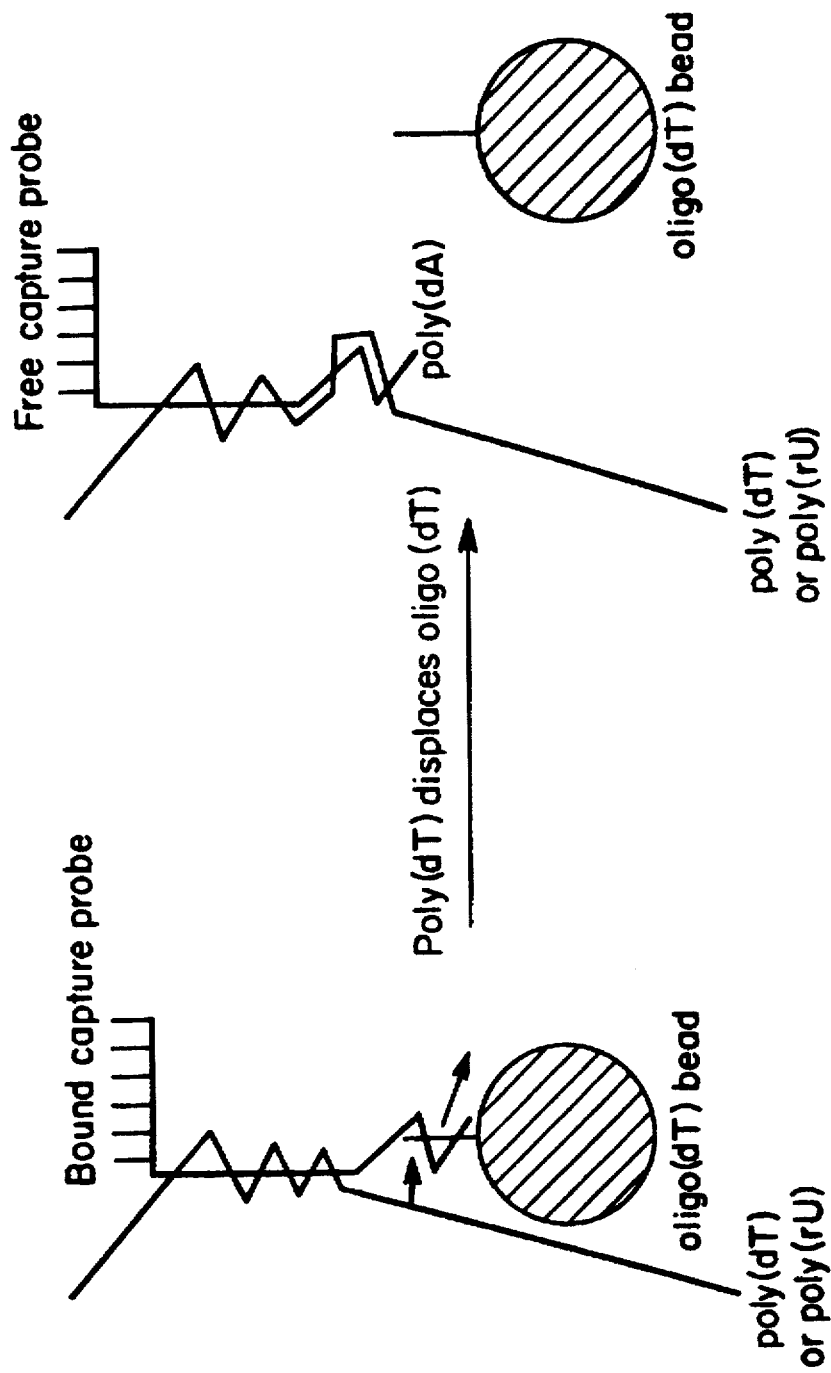
FIG. 5 is an example of release method A in which a homopolymer such as poly(dT) is used to displace the dA-tailed capture probe (potentially bound to target) from the oligo(dT) support.

It is not possible to recapture the probe-target complex on poly(dT)-nylon for detection following release method A because the poly(dA) tail is blocked by excess poly(dT). This is illustrated in FIG. 5. Two alternative recapture schemes are shown in FIG. 6. In the first model on the left side of the Figure, there are two separate capture probes, denoted CP1 and CP2. CP1 has a poly(dA) tail for RTC. GP2 has a second affinity ligand denoted X, which could be, e.g., biotin, an antigen, streptavidin, avidin, an antibody, or any other member of an affinity pair. LP is the labeled probe and the heavy line represents the target. In FIG. 6 poly(rU) was used as the displacing agent to remove the intact probe-target complex from oligo(dT) beads. Since the poly (rU) is hybridized to the poly(dA) tail of the capture probe following release method A, recapture to oligo(dT) is impossible, but capture on an anti-X solid support is possible through CP2. Anti-X is simply the complementary member of the affinity ligand X, which was defined above.

In the second model on the right, one capture probe, denoted GP1, is derivatized with two affinity ligands, poly (dA) and X. Following release with poly(rU) or poly(dT) or some other homopolymer, the target is recaptured by the second affinity ligand X on a support derivatized with anti-X.

Format 1 can be used when the assay demands that more than one specific probe be used. The labeled probe can be either generic or specific. Format 2 can be used whenever 1 specific capture probe is sufficient. The labeled probe can also be generic or specific in format 2. It is important to note that recapture on oligo(dT) is possible when poly(dA) or poly(rA) is used for displacement. However, the vast amount of solid phase required makes this a less desirable format.

In release method B, two capture probes and a detector probe are initially bound to the target, forming a capturable quarternary complex. Capture probe #1 forms a less stable hybrid to the target than capture probe #2. After one or more rounds of RTC, the support-bound probe-target complex is washed just below the Td of the probe #1, then washed at a temperature just above Td of probe #1, such that probe #1 is released, leaving a ternary {(capture probe #2):(target): (detector probe)} complex. The eluted ternary complex is then recaptured via capture probe #2, which is still hybridized to target after the above wash step and the present release step.

In release method C, RTC is used to reduce NSB as much as possible. The solid support is washed, e.g., with a regimen of low salt, followed (or preceded) by high temperature plus detergents (e.g., the present wash protocol, described above) that are fully compatible with the stability of hybrid #1 (FIG. 1), and other protocols known to be useful in reducing NSB. The solid support is washed several times at the appropriately low (mild) temperatures in release method A buffer minus the displacing agent(s). Release method C is performed at very low temperatures (even below 0° C.) in detergent-free buffers containing relatively high salt (since heat, low salt, and detergents are agents known to preferentially release nonspecifically bound molecules). The technique would be rapid, reversible, highly specific and generic.

A method of affinity background capture (ABC) which enhances the signal-to-noise ratio is also the subject of the present invention. The term "affinity background capture" refers to the capture of detector or labeled probe that is not hybridized to target. Collins, *Analytical Biochemistry*, 181: 360–370 (1989) It is a technique that is primarily useful for reducing NSB, not NSH.

In one embodiment, RTC is carried out according to the usual procedure, and a background capture probe is added to the reaction mixture. The background capture probe is characterized in that it has a nucleotide sequence which is complementary to the nucleotide sequence of the labeled detector probe, and has an affinity ligand, such as biotin. The labeled probe which has not hybridized with the target nucleic acid becomes hybridized to the background capture probe, and the {(labeled probe):(background capture probe)} complex is then removed from the reaction mixture by contacting it with a solid support which has an affinity ligand complementary to the affinity ligand on the background capture probe. The complex formed between the background capture probe and the labeled probe becomes attached to the solid support through the affinity ligand-labeled probe duplex. This method of removing noise by reducing the amount of free labeled probe improves the signal-to-noise ratio by up to 40-fold.

Figure 3:
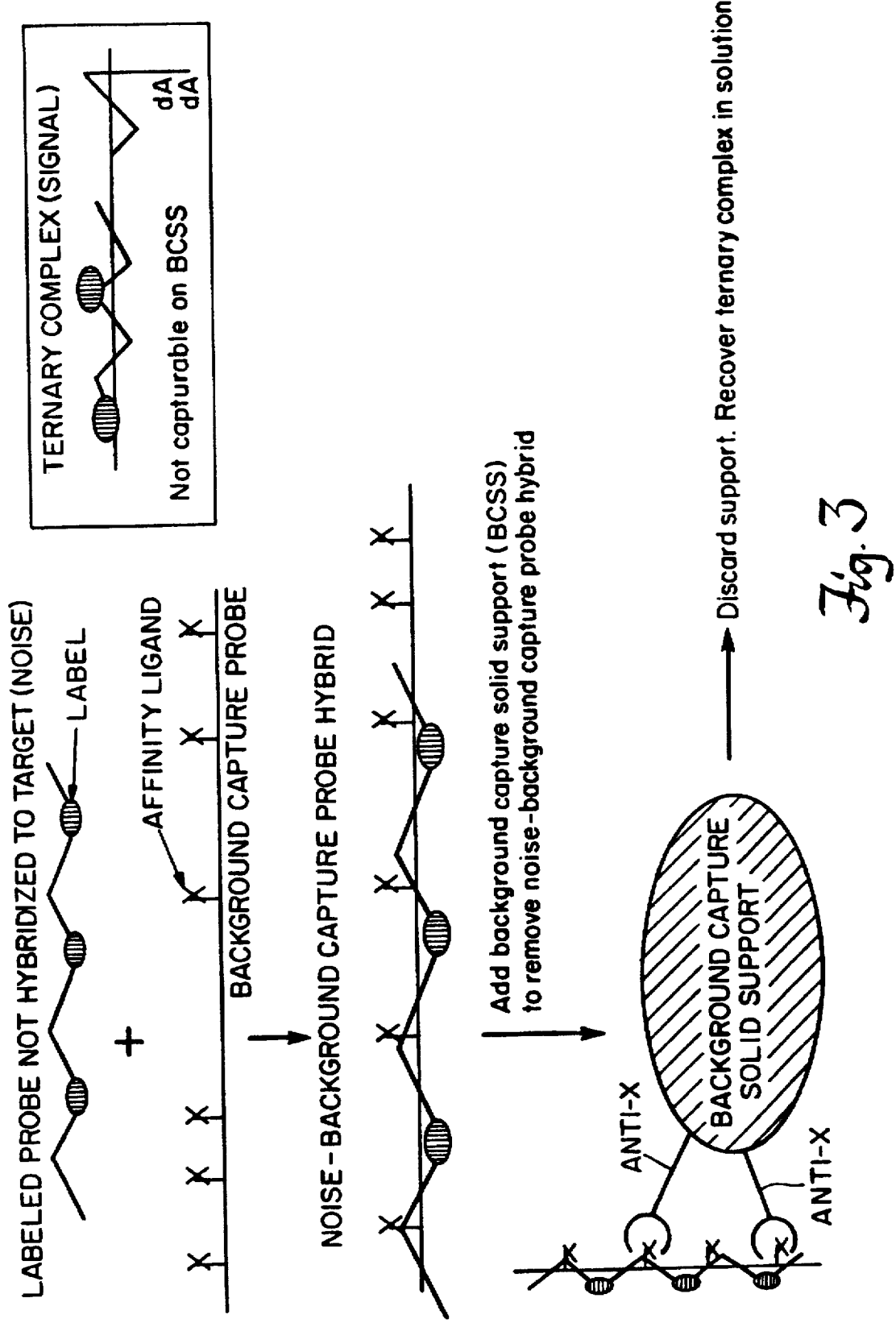
FIGS. 3 and 4 depict preferred embodiments for affinity background capture in which labeled probes not bound to target are selectively removed on an affinity support by means of background capture probes to which the labeled probes are hybridized. Target is recovered in solution.

The goal of the present invention is to achieve the same or better signal to noise enhancement (e.g., compared to that achieved by the method described by Collins in *Analytical Biochem.*, 189: 360–370 (1989) with a more generalizable background capture technique, one which does not require the detector probe to contain any particular nucleotides or to be an oligonucleotide. In another preferred background capture method, excess (unhybridized) detector probe is removed by hybridizing it with a vast molar excess of the background capture probe in solution and capture of the formed complex onto a suitable solid support bearing a receptor for an affinity ligand. The process is schematically illustrated in FIG. 3. In the upper left-hand corner of FIG. 3, there is a labeled probe that is not hybridized to target. This is the noise that background capture is going to remove. Below the labeled probe is the actual background capture probe, which is represented as a straight line with affinity ligands (X's) attached to the probe. These affinity ligands can be nucleic acid sequences, antigens, avidin, streptavidin, antibodies etc. The background capture probes are used in molar excess of the reporter (labeled) probe, and thus drive the majority of the free labeled probes into an affinity-labeled duplex pictured in the middle of the figure.

The ternary complex in the box on the right (FIG. 3), on the other hand, is mostly resistant to hybridization with the background capture probe by virtue of its being already hybridized to the labeled probe. There is, however, the possibility that the background capture probe could hybridize to the labeled probe bound to the target and actively displace the target, either partially or completely. In either case, the target would become "labeled" with the affinity ligand and would be lost on the background capture solid support with the background. Optimally, there would be maximal hybridization of the background capture probe to the labeled probe and minimal hybridization of the background capture probe to the ternary complex.

At the bottom of FIG. 3, the hybrid between the "noise" (excess labeled probe) and the background capture probe is being attracted by the anti-X on the background capture solid support. Anti-X is the other member of the affinity pair, i.e. streptavidin if X-biotin. The ternary complex, by virtue of the fact that it does not possess a ligand X, is incapable of binding to the background capture support. It is recovered in the solution phase after the solid phase containing the noise is discarded. This illustrates one of the principle advantages of background capture over target capture, namely that neither washes nor elutions are required since the target is recovered in the fluid phase.

Figure 4:
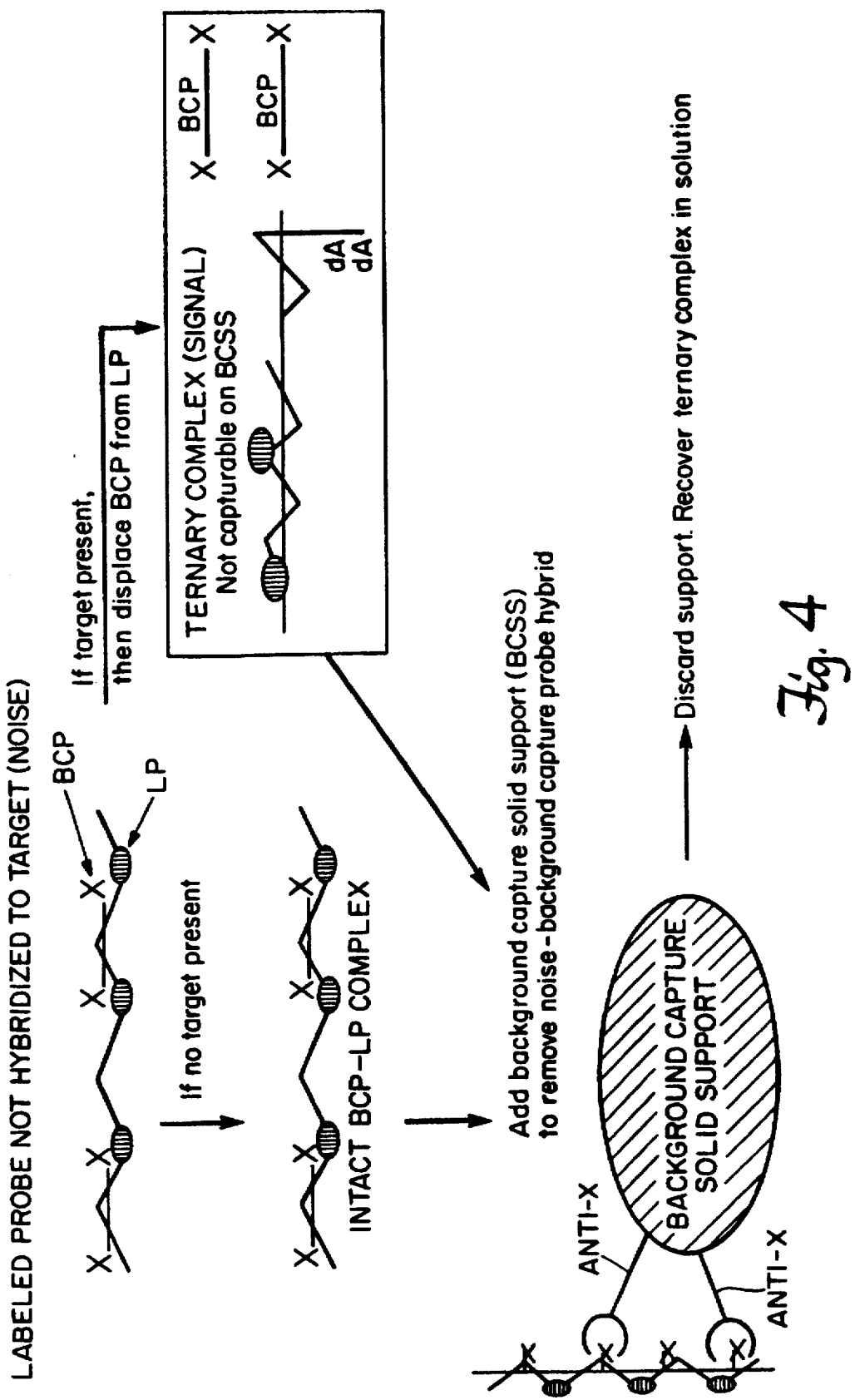

Another preferred method of affinity background capture employs displacement hybridization and is schematically illustrated in FIG. 4. A molar excess of one or more affinity labeled oligonucleotides is hybridized to a reporter probe (preferably a riboprobe) prior to the assay. This produces the reporter probe-background capture probe complex shown in the upper left corner of FIG. 4. This {(reporter probe): (background capture probe)} complex is added to the analyte. If present, the target hybridizes to a region of the detector probe adjacent to the background capture probe and displaces it from the detector probe either by virtue of the target's larger size or by virtue of the greater stability of dsRNA as compared to RNA-DNA in the hybridization buffer or both. Thus, as indicated on the right of FIG. 4, the ternary complex is formed and the background capture probes are displaced from the labeled probe. On the left in the center of FIG. 4, detector probes not hybridized to target remain hybridized to background capture oligonucleotides. The detector probes not hybridized to target are captured via the ligand and on the background capture probes on the background capture support and discarded (FIG. 4, bottom left). The target is recovered in the liquid phase for further target capture or detection (FIG. 4, bottom right). The background capture is ideally done after one or two rounds of target capture to reduce the concentration of affinity ligand to be trapped on the background capture support. This reduces the cost of that support and improves the efficiency of the process.

The high-temperature washing method, the release methods and the affinity background capture methods described herein all reduce the amount of NSH and/or NSB in the hybridization assay system. The signal-to-noise ratio is increased by several orders by magnitude using one or more of these methods after a RTC hybridization assay.

The invention may be more clearly understood with reference to the following examples which are not intended to be limiting in any way.

EXEMPLIFICATION

Materials and Methods

The basic Reversible Target Capture (RTC) procedure used in these examples is described in detail in European Patent Application No. 87309308.2 and Collins, *Analytical Biochemistry*, 181:345–359 and 360–370 (1989) The probe sequences used in the examples are shown in Table 1.

The signal/noise enhancement was computed as (S1/S2)/(N1/N2), where S1=signal with the wash, S2=signal without the wash, N1=noise with the wash, N2=noise without the wash. Each set of elution conditions has its own control without a TMA-phosphate wash with a S/N enhancement of 1.0. All elutions were preceded by a low salt wash. Chemical elution and the no salt buffers contained no detergent at all, while thermal elution buffer contained 0.5% sodium lauroyl sarcosine.

TABLE 1

Sequences of oligonucleotides used in the examples

| Sequence # (target) | Sequence (5' - - - 3') |
|---|---|
| 773 (Listeria 16S rRNA) | TGTCCCCGAAGGGAAAGCTCTGTCTCCAGAGTGGT |
| 787 (E. coli 16S rRNA) | TCAATGAGCAAAGGTATTAACTTTACTCCCTTCCT |
| 839 (HIV RNA) | TTTAATTCTTTATTCATAGATTCTACTACTCCTTGACTTT |
| 1199 (HIV RNA) | CTTCCCTAAAAAATTAGCCTGTCTCTCAGTACAATCTTTC |
| 1780 (N. gon. 16S rRNA) | ATTCCGCACATCTCAAAACCAGGT |

EXAMPLE 1

Use of a high temperature wash step to Complement RTC's NSB-reducing power

The following protocol was used to measure the efficacy of a high temperature 3.0M TMA phosphate wash in reducing NSB in RTC hybridization assays. Two hybridization reactions were set up: one contained $10^6$ Listeria/ml and the other $3 \times 10^7$ Campylobacter/ml. Both contained the generic eubacterial $^{32}$P-labeled riboprobe and 0.1 µg/ml of Listeria-specific capture probe (#773). Hybridization was for 15 minutes in 0.5M GTC at 55 degrees and capture was with two volumes of beads containing 1M NaCl at 37° C. The beads were washed three times with 0.5M GuSCN bead wash buffer. The beads were split into equal aliquots. Some were given a TMA phosphate wash for 2 minutes with preheated buffers and others were washed with bead wash buffer. Finally, all samples were incubated with one of three different elution protocols: 2.5M GuSCN at 37° C., no salt (TE) at 37°, and thermal elution at 62° C. The Listeria signal samples were scintillation counted to determine the effect of TMA phosphate washing on signal. The control (noise) samples were autoradiographed and scanned by densitometry to measure the effect of TMA phosphate washing on noise. The results of a typical experiment are shown in Table 2.

TABLE 2

Reduction of NSB with TMA phosphate wash

| High Temperature Wash | Elution condition | Signal (CPM) | Noise (Area) | S/N enhancement |
|---|---|---|---|---|
| No | Chemical | 3257 | 45.5 | 1.0 |
| Yes | Chemical | 2417 | 1.7 | 20.3 |
| No | No salt | 3366 | 38.8 | 1.0 |
| Yes | No salt | 2274 | 1.1 | 23.5 |
| No | thermal | 3084 | 78.0 | 1.0 |
| Yes | thermal | 2073 | 0.48 | 109.0 |

The signals were measured in cpm and the noise values were measured in areas under the autoradiographic tracings.

From the data of Table 2 it is clear that any elution buffer can be used with the TMA-phosphate wash to improve the signal/noise assay by reducing NSB up to about 20-fold.

In approximately 3M TMA phosphate, the dissociation temperature has been found to be a linear function of length, but not a function of GC content (as in TMA Cl). Thus all probes of approximately 25 nucleotides in length (optimal for RTC) have the same Td regardless of GC content. In addition, it has been found that double-stranded RNA oligo hybrids dissociate at approximately the same temperature as DNA-RNA hybrids with the same length in 3–5M TMA salts.

In approximately 3M TMA phosphate the dissociation curves are very clean (<1% unmelted hybrid at Td+5 degrees) and very sharp (breadth about 1–3 degrees), allowing maximal discrimination between correctly and incorrectly formed hybrids because a mismatched sequence which dissociates 5°–20° C. below the $T_d$ of the probe-target complex has virtually completely (>99%) dissociated before the probe-target complex has begun to dissociate. The discrimination is not nearly as good in GuSCN or NaCl where the breadth of the curves is as high as 10° C. degrees and the melting is rarely cleaner than 95–97% even at $T_d+20°$ C. With NaCl or GuSCN, the dissociation curves for target and pseudotarget usually have some and sometimes even have a significant overlap, thus reducing the total discrimination between the two sequences. Thus specificity with double stranded RNAs, double-stranded DNAs, and RNA-DNA hybrids should be exceptional in TMA phosphate as compared to NaCl or GuSCN. This exceptional specificity has been verified with a *Neisseria gonorrhea* 16S rRNA target system. With a 24mer DNA probe (#1780, Table 1) containing only two mismatches with *N. meningitis* rRNA, about a 350,000-fold discrimination between the target and the pseudotarget has been achieved with RTC employing a high-temperature wash with TMA phosphate.

EXAMPLE 2

One Round of Reversible Target Capture with High-Temperature Wash and Release Method A

A.

The following example illustrates how incorporation of the high-temperature wash step of Example 1 with release method A provides picogram sensitivity in just one round of capture on magnetic particles. This is approximately 100 times better sensitivity than can normally be achieved in an unamplified system with just one round of capture with oligonucleotide capture probes. Morrissey and Collins, (1989) *Molecular and Cellular Probes*, 3, 189–207.

A 3 kb synthetic RNA HIV-positive control was serially diluted into T blast lysate ($2.8 \times 10^6$ cells/ml, final conc.) and probed with HIV specific 839 and 1199 capture probes and a $^{32}$p-labeled HIV-specific riboprobe. After a 15 minute hybridization, 2 volumes of magnetic particles were added and capture allowed to occur for 5 minutes. The beads were washed with 1M GuSCN wash buffer and then washed as described in Example 1 with TMA phosphate buffer at 60° C. for 5 minutes. They were extensively washed with a buffer containing 0.15M NaCl, 0.1M Tris-HCl (pH 7.5), 10 mM EDTA, 0.5% Tween-20 at 37° C. and then released with the same buffer containing 1.67 μg/ml poly(dT)$_{300}$ at 37° C. for 2 minutes. The samples were then scintillation counted. The detection limit (two standard deviations above the average of the negative controls) was 2 picograms (2 attomoles) of HIV positive control.

If an assay requires only pg sensitivity, it may be possible to do just a single round of capture with a TMA phosphate wash step and release method A or similar format and reserve triple capture (and enhancements) for assays requiring femtogram sensitivity or less.

EXAMPLE 3

Release Method A with recapture

The following example illustrates release method A using one capture probe containing two affinity ligands (format 2, FIG. 6). For this experiment, Listeria-specific probe #773-dA$_{160}$ was retailed with bio-14odATP (Bethesda Research Labs). Two hybridizations were set up. One contained $1.5 \times 10^5$ Listeria and $5 \times 10^6$ Campylobacter while the other contained only $5 \times 10$ Campylobacter. The capture probe was used at 0.5 μg/ml and the hybridization was done in 4.0M GuCl, 0.6M GuSCN at 37° C. After capture with one volume of beads containing 5M urea, and washing in a wash buffer containing 4M GuCl, the beads were washed for 5 minutes in wash buffer containing 0.15M NaCl at 37° C. They were divided into three aliquots. One was counted, one was released using release method A as described in Example 2 with 5 μg/ml poly(dT), and the other was released with 10 μg/ml poly(rU) (Pharmacia) in the 0.15M NaCl wash buffer for 5 minutes at 37° C. Following release, 100 μl of streptavidin-coated magnetic particles (Biomag™ from Advanced Magnetics) were added to recapture the targets. The streptavidin Biomag™ solid support was prepared by coupling streptavidin to NH$_2$-derivatized Biomag™ or to COOH-derivatized Biomag™ using carbodiimide activation. Lund et al., *Nucleic Acids Research*, 16: 10861–10880 (1988). The beads were filtered onto nitrocellulose filters. All samples were saved and scintillation counted. The results are shown in Table 3.

TABLE 3

Successful recapture on streptavidin-Biomag after the release step

| Fraction: | CPM Signal | | CPM Noise | |
|---|---|---|---|---|
| | dT | rU | dT | rU |
| Did not elute from first beads | 7768 | 12693 | 208 | 200 |
| Did not rebind to SA beads | 43 | 62 | ND | ND |
| SA beads | 8382 | 7302 | ND | ND |

'ND∝ means not detectable over the machine background of 20 cpm after a 10 minute count.
'dT∝ and 'rU∝ refer to release with poly (dT) or poly (rU) respectively.
'SA∝ beads refers to streptavidin Biomag.

On the final set of beads the data are essentially the same for both elution schemes. At the concentrations employed, elution with poly(dT) was slightly more efficient that with poly(rU). The release step left about 99% of the background on the oligo(dT) beads and no detectable ('ND') radioactivity rebound to the streptavidin beads in the controls. Recapture of the probe-target complex on streptavidin beads was more than 99% efficient.

EXAMPLE 4

RTC with Affinity Background Capture

In this method, *E. coli* 16S rRNA was used as the target in the test sample and a sample containing no target was used as the control. The 3' $^{32}$p labeled eubacterial riboprobe was used as the detector probe, and probe #787 (Table 1) was used as the *E. coil*-specific capture probe. A background capture riboprobe complementary to the reporter probe was prepared by cutting the pGEM3 (16S) vector with SmaI and transcribing with T7 polymerase in the presence of bioUTP. A background capture solid support, streptavidin-Biomag™, was prepared by coupling streptavidin to NH$_2$-derivatized Biomag™or to COOH-derivated Biomag as described in Example 3.

The procedure used for background capture is set out in Table 4 below.

TABLE 4

RTC with Affinity Background Capture

| STEP | |
|---|---|
| Formation of ternary complexes | 55° C.; 15 min; 0.5M GuSCN |
| Signal Capture | Biomag dT beads, 5 min., 37° C. |
| Wash | 0.5M GuSCN, 37° C. |
| Thermal Elution | thermal elution buffer 65° C. (0.5M NaCl) |
| Hybridization of background capture riboprobe to the excess detector probe | thermal elution buffer at 65° C. for 7 min. |
| Background Capture | thermal elution buffer at 37° C. for 5 min, on streptavidin-Biomag beads. |
| Final Signal Capture | poly dT nitrocellulose filter |
| Detection | autoradiography (densitometry); scintillation counter |

The enhancement of the signal to noise ratio was determined by the following equation:

E(S/N)=signal⁺cpm/signal⁻cpm)/(noise⁺peak height/noise⁻peak height)

E(S/N)=(115489/210659)/(742/53918)=39.7
S=Signal
N=Noise
+=With background capture
−=Without background capture
E(S/N)=Signal to Noise Enhancement Noise was reduced over 70-fold by employing background capture and RTC as compared to two rounds of RTC without background capture, while only about 45% of the signal was lost, presumably to displacement of the labeled probe bound to target by the background capture riboprobe.

EXAMPLE 5

Release Methods B and C

This example defines protocols for release methods B and C. The following discussion refers to FIG. 2. Consider the following specific example for the conditions labeled w (washing step) and r (release step). The process of chemical elution as described by Collins in *Analytical Biochemistry*, 181, 345–359 involves washing the oligo(dT)14 beads in 0.5–1.0M GuSCN and then eluting in 2.0–2.5M GuSCN (this disrupts only hybrid #1 in FIG. 1). These conditions are required by the rather broad melting profile of the poly(dA)-oligo(dT) hybrid in GuSCN. This 1–2M increase in the concentration of GuSCN is equivalent to 12.5°–25° C. of heat (the average chaotropic index of GuSCN for dsDNA is 12.5 degrees per Molar). Thermal melting in tetraalkylammonium salts, however, has been reported to have a breadth of 1° to 2° C. Melchior and von Hippel, (1973) *Proc. NaCl. Acad. Sci.*, 70, 298–302. Thus, by washing the beads containing probe-target complex at $T_d-1$ or $T_d-2°$ C. (w" conditions) and then eluting at $T_d+2°$ C. degrees (r), the beads would be subjected to only a differential change in physical condition and theoretically much less background would be eluted than with prior art wash conditions (w) and release conditions (r).

Since release method B would disrupt hybrid #2 in FIG. 1, its reversibility would require rehybridization of the original capture probe or rehybridization of a new capture probe to the target. This would, however, be very undesirable in a rapid assay format. Accordingly, the following scheme is preferred for release B. A probe-target quaternary complex would be formed similar to the one in FIG. 6 (top left) with two capture probes and a detector probe(s). One of the capture probes would preferably form a somewhat more stable hybrid with the target than the other capture probe. For example, suppose GP2 forms the more stable hybrid in a tetraalkylammonium salt because it is longer than CP1. In the preferred format, all three types of probes would by hybridized to the target and the target captured onto the oligo(dT)-bead. The bead would be washed and the process optionally repeated. The bead would be washed at a temperature that is $T_d-1$ or $T_d-2°$ C. below the hybrid between CP1 and the target. This would optimally be in a tetraalkylammonium salt buffer, in which the oligo(dT)-poly(dA) hybrid has a special stability and in which the optimal temperature of wash is independent of GC content and essentially independent of the type of double-stranded hybrid formed. This would be optimal for reducing NSH of all of the hybrids formed and reducing NSB (if it is a high temperature wash). The target would be released by dissociating the hybrid between CP1 and the target by washing at approximately $T_d+2$ degrees, leaving the capture probe bound to the bead. The intact ternary {(labeled probe): (target):(capture probe #2)} complex would then be captured on an anti-X support for further background reduction. The tetraalkylammonium wash could be done at a higher temperature on the anti-X support for further NSH and NSB reduction (if desired), prior to yet another type of smart release prior to detection.

Alternatively, the (target):(capture probe #2) hybrid could be the weak link in the quaternary complex, which would be captured on the anti-X support first, washed at Td−2, released with release method B at $T_d+2$, and recaptured any number of times on oligo(dT). Optimally, a wash step at a higher temperature and then release method A could be done prior to a solution phase detection or release method A could be done under release method C conditions (below) prior to solution phase detection.

Figure 2:
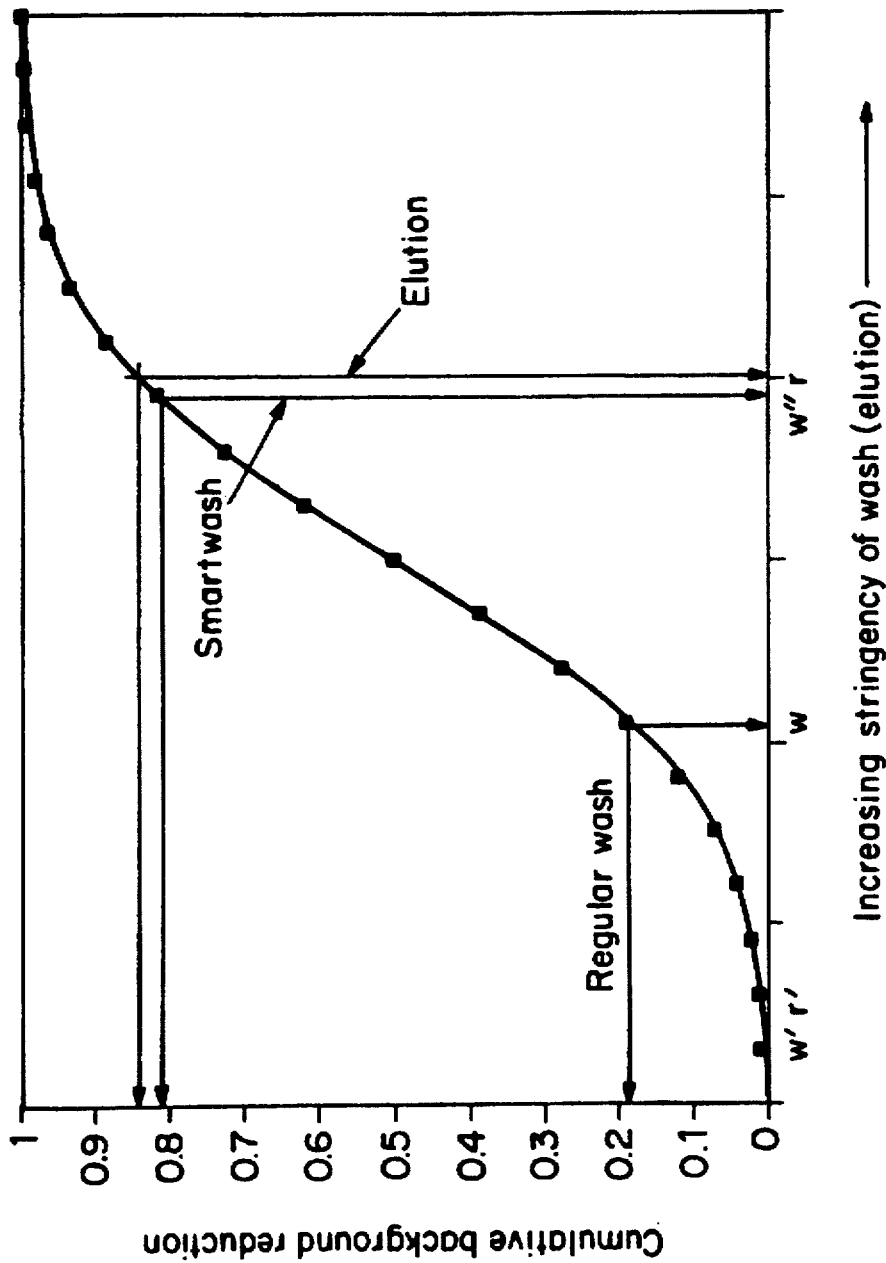
FIG. 2 depicts a theoretical cumulative profile of background (NSH or NSB) released from a solid support as a function of the intensity of washing or elution conditions. Possible wash and elution conditions are illustrated for methods referred to as release methods B and C.

In FIG. 2, release method C conditions are graphically defined as wash (w') and release (r') conditions that are in the early part of the cumulative elution of background profile, where dy/dx is essentially zero. However, release method G would optimally be done after regular wash (w) and the present wash (w") described in Example 1, had already been done. The background that would normally elute under r' conditions should be almost completely removed by those washing protocols. The conditions for release method G require only that all hybrids in the complex be stable to conditions w, w', and w". The use of tetraalkylammonium salts and high temperatures has already been shown to be an acceptable w" condition. Other stringent, background reducing conditions such as low salt (w or w") washes could be employed prior to release method C.

Optimally, release method C would be done with no detergent at very low temperatures and in high (non-chaotropic) salt to minimize the release of background (r' release conditions), immediately following washing under closely related w' conditions (as in release method B). The trigger to cause release would optimally be a process such as displacement hybridization with poly(dT) or poly(rU), which is highly specific for disruption of hybrid #1 (FIG. 1) and highly insensitive to temperature and salt. The target could then be recaptured via a second capture probe or a second ligand on the displaced capture probe as defined above.

In addition, with all of the methods listed above, the final detection can be in the solution phase after the final, highly specific release reaction. Thus either during or prior to solution phase detection, homogenous methods by which a detector probe bound to target can be distinguished from an unbound detector probe could be employed for additional specificity and background reduction. Such methods include the detection of energy transfer (Heller et al., EPO Application No. 0070 685) and various target-dependent enzymatic reactions such as ligation, and cleavage of a less active precursor to form a more active enzyme substrate (Stefano, European Patent Application No. 89310066.9).

Equivalents

Those skilled in the art will recognize, or be able to ascertain that the invention is not using more than routine experimentation, many equivalents to the specific embodiments of the invention described herein. Such equivalents are intended to be encompassed by the following claims.

We claim:

1. A method for increasing the signal to noise ratio in a capture/detection hybridization assay, comprising:
    a) providing a quaternary complex comprising:
        i) a target nucleic acid having a first and a second region;
        ii) a capture probe comprising a first region which is a homopolynucleotide (dA) tail, and a second region which is perfectly complementary to the first region of the target nucleic acid, the second region having a length of from 24 to 40 nucleotides;
        iii) a detection probe which is complementary to the second region of the target nucleic acid; and
        iv) a homooligonucleotide of (dT) bound to a solid support, the homooligonucleotide of (dT) having a length of from 10 to 14 nucleotides; and
    b) washing the complex of step a) with a solution comprising a tetramethylammonium salt, having a molarity of about 3.0, at a temperature of from 60° C. to 70° C. to elute non-specifically bound detector probe.

2. A method for increasing the signal to noise ratio in a capture/detection hybridization assay, comprising:
    a) providing a quaternary complex comprising:
        i) a target nucleic acid having a first and a second region;
        ii) a capture probe comprising a first region which is a homopolynucleotide (dT) tail, and a second region which is perfectly complementary to the first region of the target nucleic acid, the second region having a length of from 24 to 40 nucleotides;
        iii) a detection probe which is complementary to the second region of the target nucleic acid; and
        iv) a homooligonucleotide of (dA) bound to a solid support, the homooligonucleotide of (dA) having a length of from 10 to 14 nucleotides; and
    b) washing the complex of step a) with a solution comprising a tetramethylammonium salt, having a molarity of about 3.0, at a temperature of from 60° C. to 70° C. to elute non-specifically bound detector probe.

* * * * *